United States Patent [19]

Seitz

[11] Patent Number: 4,862,743

[45] Date of Patent: Sep. 5, 1989

[54] DEVICE FOR MEASURING THE AREAL DISTRIBUTION OF COMPRESSIVE FORCES

[76] Inventor: Peter Seitz, Mohlstrasse 28, D-8000 Munchen 80, Fed. Rep. of Germany

[21] Appl. No.: 156,244

[22] Filed: Feb. 16, 1988

[30] Foreign Application Priority Data

Feb. 16, 1987 [DE] Fed. Rep. of Germany ....... 3704870

[51] Int. Cl.⁴ .............................................. G01D 7/02
[52] U.S. Cl. .................................. 73/172; 73/862.04; 128/779
[58] Field of Search ................ 73/862.04, 862.64, 172; 128/779

[56] References Cited

U.S. PATENT DOCUMENTS

| 4,262,532 | 4/1981 | Butler et al. | |
| 4,437,138 | 3/1984 | Nicol | 361/283 |
| 4,458,537 | 7/1984 | Bell et al. | 73/718 |
| 4,644,801 | 2/1987 | Kustanovich | 361/283 |
| 4,745,930 | 5/1988 | Confer | 128/779 |

FOREIGN PATENT DOCUMENTS

| 2448398 | 10/1974 | Fed. Rep. of Germany . |
| 2529475 | 7/1975 | Fed. Rep. of Germany . |
| 2800844 | 1/1978 | Fed. Rep. of Germany . |
| 2831938 | 7/1978 | Fed. Rep. of Germany . |
| 3025362 | 4/1980 | Fed. Rep. of Germany . |
| 3411528 | 3/1984 | Fed. Rep. of Germany . |
| 0172784 | 8/1985 | Fed. Rep. of Germany . |

OTHER PUBLICATIONS

"New Advances in Printed Circuits", Nov. 22, 1948, Misc. Publication 192, p. 15.

Primary Examiner—Joseph A. Orsino
Assistant Examiner—Hollis T. Chen
Attorney, Agent, or Firm—Burgess, Ryan & Wayne

[57] ABSTRACT

A device is disclosed for measuring the areal distribution of compressive forces which act substantially vertically with respect to a deformable measuring surface. A matrix arrangement of force sensors is provided, each of which is formed as a capacitance at crossings of substantially perpendicular conductor paths. The conductor paths are fixed on the opposed surfaces of an elastically deformable area-type dielectric and adapted to be connected by conductive elements to evaluator electronics. The conductor paths are printed on plastic substrate films.

20 Claims, 7 Drawing Sheets

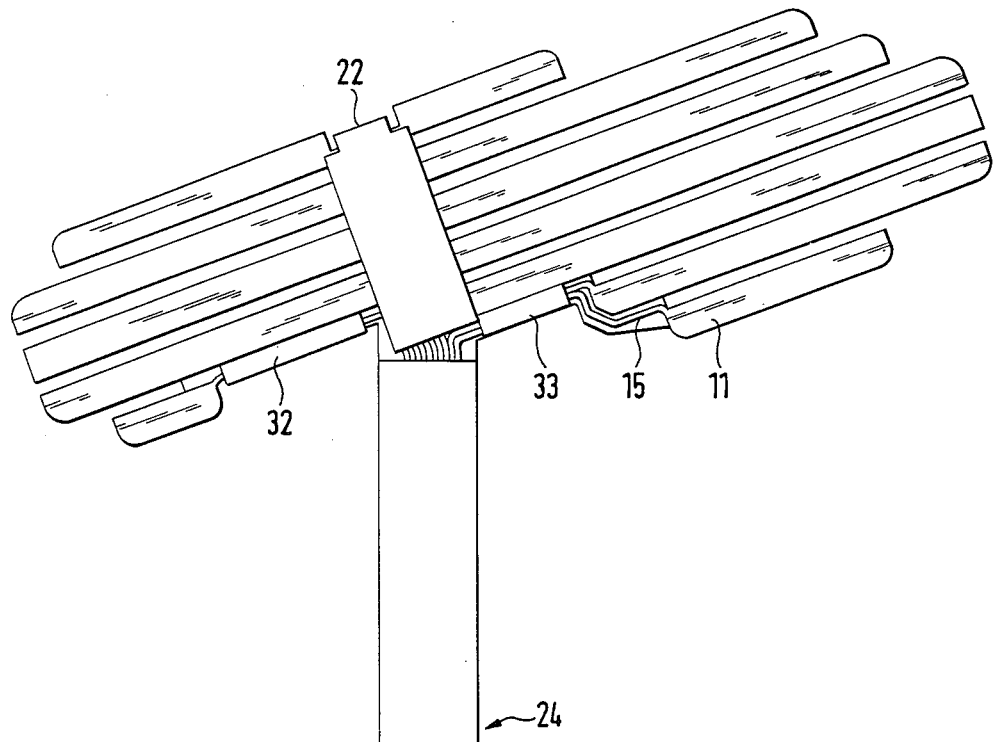
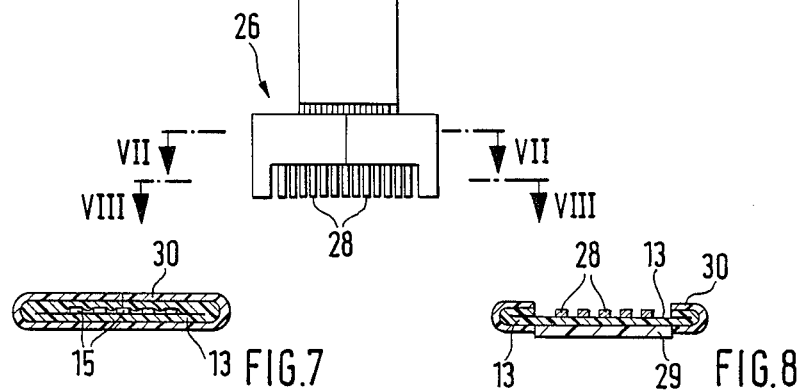
FIG. 6
FIG. 7  FIG. 8

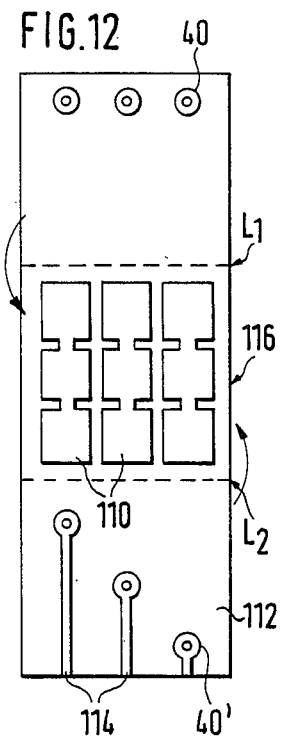
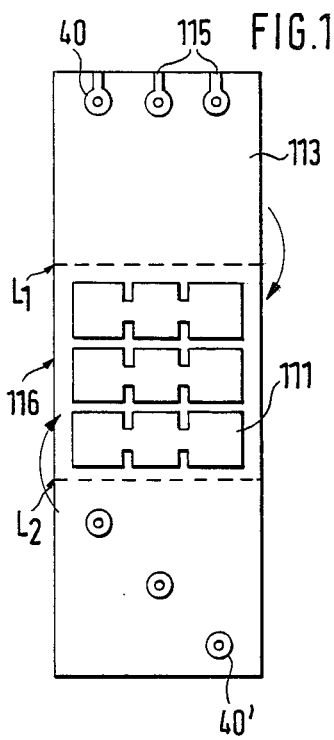
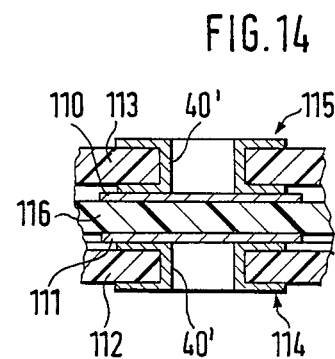
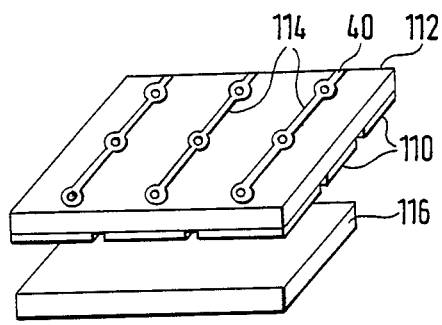
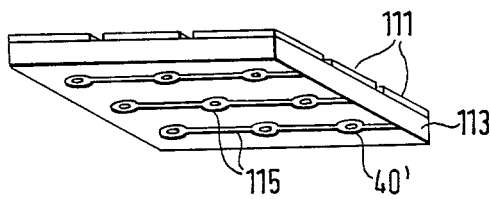

DEVICE FOR MEASURING THE AREAL DISTRIBUTION OF COMPRESSIVE FORCES

FIELD OF THE INVENTION

The invention relates to a device for measuring the areal distribution of compressive forces acting substantially perpendicularly on a deformable measuring surface, comprising a matrix arrangement of force sensors formed respectively by capacitances at crossings between two groups of capacitor element arrays printed on a plastic substrate film and fixed on the opposed surfaces of an elastically deformable area-type dielectric and adapted to be connected by leads to evaluator electronics.

BACKGROUND OF THE INVENTION

DE-OS 24 48 398 and DE-OS 28 00 844 disclose measuring devices with which elastic mats including capacitor areas are provided to enable measurements of the normal forces acting on the mats. However, an areal distribution of the compressive forces cannot be resolved by these devices.

A measuring arrangement for the areal distribution of compressive forces is known from DE-OS 25 29 475 and this will be especially referred to here. The mat according to the invention can be operated with evaluating electronics shown in that publication and which can be used with the present invention. Accordingly, the electronics for evaluation will not be described in greater detail herein.

Starting from DE-OS 25 29 475 mentioned above, a device of the kind recited initially has become known from DE-PS 30 25 362. That device reveals a special concept of the conductor paths, a concept chosen because simple conductor paths fixed on an elastically deformable area-type dielectric allegedly involve poor electrical characteristics (non-linearity, hysteresis), as well as poor mechanical properties (signs of relaxation, fatigue of material, limited flexibility). Furthermore, such publication reveals that the devices are useful exclusively on a hard, planar background. It is also pointed out in that publication that such simple arrangements bring mechanical tight coupling with adjacent capacitors. It is suggested in the publication that those disadvantages be avoided by applying special grid conductor paths in a special manner. Yet, that arrangement is extremely complicated and especially unsuitable for use, for example, when a measuring arrangement is to be made which is to be worn in a shoe, as regards the flexibility. Problems relating to flexibility also occur when the measuring surface is placed on a motor vehicle seat (to measure the sitting behavior of test persons). Moreover, mass production of such a measuring mat is almost impossible because of the great expenditure involved.

A measuring arrangement of the kind mentioned initially is known also from DE-OS 34 11 528, and it likewise is aimed at improving the electrical and mechanical properties. In that publication too, it is stated that strips of metalized plastic sheeting or film were not suitable as conductor paths. It is suggested in the publicaton to sever the individual measuring areas obtained at the points of intersection of the conductor paths by cuts in order to achieve mechanical uncoupling. However, this proposal also causes high production costs and moreover, leads to high susceptibility to breaking of the arrangement.

OBJECTS AND SUMMARY OF THE INVENTION

Starting from the prior art presented above, it is an object of the instant invention to develop a device of the kind specified initially such that a precise and yet strong measuring arrangement of great flexibility is attainable at limited expenditure.

This object is met by the features described herein and indicated in the claims.

According to one aspect of the invention, a plurality of force detector means are provided. Each of these force detector means includes a capacitor. Each capacitor is formed by capacitor elements, a first group of capacitor elements being arranged on one surface of an elastically deformable area-type dielectric, and a second group of capacitor elements being arranged on a second surface thereof. The capacitors thus are formed at the points of intersection of the first and second capacitor elements. In this manner, a matrix arrangement of force detector means is obtained. The groups of capacitor elements are connected by leads to electronic equipment for evaluation. Together with the leads, the capacitor elements are printed on substrate sheeting or films made of plastics.

Surprisingly, it is shown by the present invention that, in contrast to the opinion held so far, simple conductor paths indeed are useful, provided they are printed on a plastic substrate film. This means that grid structures need not be provided in order to bring about sufficient mechanical uncoupling and good electrical characteristics at the same time.

Another essential aspect of the instant invention resides in the particularly favorable manufacture afforded by the use of printed conductor paths and shielding areas. With appropriate configurations, as set out in the claims, this permits, in the simplest manner, the production of measuring mats which are especially well protected against interference and which involve extremely little effort in manual work. The durability of the arrangement is greatly improved as compared to proposals known so far.

The leads are made of a synthetic resin with a metal filler, preferably a silver-filled synthetic resin. That material has especially good self-healing properties so that any fractures occurring under a load disappear automatically in the course of time.

A preferred variant of the invention has the capacitor elements and the associated leads arranged on two different sides of the substrate film, the connection between leads and capacitor elements being established by through contacts, as already known with printed circuit boards. The connection between the leads and capacitor elements thus is formed by interior linings of recesses extending all the way through the substrate films. These interior linings are made of the same material as the capacitor elements and the leads, respectively.

If a very high resolution is desirable (a great number of capacitor elements per unit area), it may happen that the capacitor elements may lie too closely together. In that event, it is advantageous to provide different measuring mat planes, each plane carrying spaced capacitor elements and the capacitor elements in the various planes being offset with respect to one another such that a projection of all capacitor elements, one on top of the other, will afford a continuous measuring surface.

If a structure is desired which is especially well protected against any electrical interference, it is advantageous to provide shielding areas which afford an electrical shield toward the outside of the capacitor elements and of the leads too, if desired. In this context, it is advantageous if shielding faces or areas are printed on the substrate films on the side thereof which is opposed to the capacitor elements so that they will cover the capacitor elements and the leads as well, if desired.

If a rather stiff substrate film is chosen (for instance, of polyvinylchloride), it is advantageous to sever the same, at least section-wise, between the capacitor elements.

An essential field of application of the device according to the invention is the measuring of forces acting on the sole of the foot during walking, running, and standing. If the device according to the invention is intended to be placed in a shoe, the object recited above is met by a device which has the measuring surface adapted to the shape of a footprint and is insertable in the shoe of a test person. In this case, the capacitor elements are arranged in rows, and one set of capacitor elements runs transversely of the longitudinal axis of the foot, while the other set of capacitor elements extends parallel to the longitudinal axis of the foot. In the area of the tuberositas ossis navicularis, the leads preferably are passed out of the shoe, together with a strip of substrate film, presenting a flat cable for connection. The resulting arrangement can be produced very easily and at low cost and yet, it is very durable and, therefore, suitable for permanent use, such as in a hospital or by an orthopedist.

BRIEF DESCRIPTION OF THE DRAWINGS

Further essential details of the invention may be gathered from the subclaims, and the description below of preferred embodiments of the invention which will be described with reference to illustrations.

FIG. 6 shows an arrangement according to FIG. 2 in the state of production, as the arrangement shown in FIG. 5;

FIG. 7 is a cross-sectional view taken along line VII—VII in FIG. 6;

FIG. 8 is a cross-sectional view taken along line VIII—VIII in FIG. 6;

FIG. 12 shows a top plan view of a second preferred embodiment of the invention (on unfinished sheeting);

FIG. 13 shows a bottom plan view of the embodiment of FIG. 12;

FIG. 14 shows a cross-sectional view through a completely assembled device of FIG. 12; and FIG. 15 is a perspective, diagrammatic, blown-apart view of a third preferred embodiment of the invention.

DESCRIPTION OF THE PREFERRED EMBODIMENTS

A preferred embodiment of the invention will be described below, which relates to a measuring surface to be placed in a shoe. The method of making the device likewise is disclosed in the specification below and it too, is considered essential to the invention.

In making this preferred embodiment, substrate PVC films 12 and 13 are provided. It is surprising that PVC is suitable as the basic material of the substrate films 12, 13. On one surface of films 12 and 13, elements are printed in the form of conductor paths 10 and 11, and conductive leads in the form of conductive elements 14 and 15, merging into the capacitor elements. Corresponding shielding areas 17 and 18 are printed on the other surface of each PVC film.

The conductive material printed on each substrate film is a metal-filled synthetic resin, the metal filling preferably being comprised substantially of silver. The silver preferably is provided in the form of microscopic filaments, as this has the consequence that "self-healing", in case a fracture should occur, may happen by simple heating, whereby the "filaments" may become rearranged.

Figure 1:
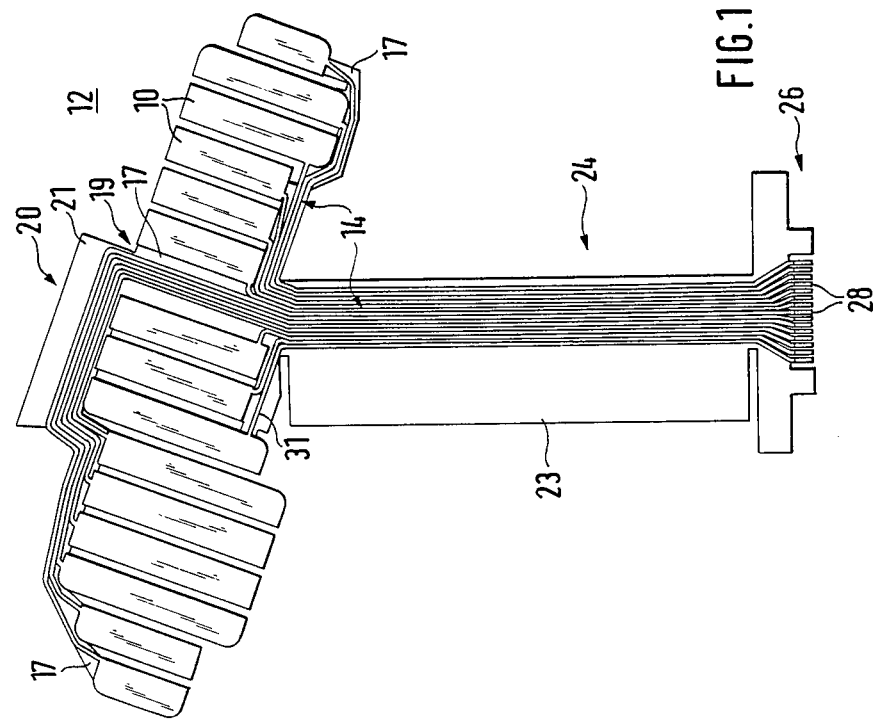
FIG. 1 shows a substrate film after the printing of conductor paths on the same.

The plane shown in FIG. 1 comprises conductor paths 10, which are oriented traversely of the longitudinal axis of the foot, one of the conductor paths being left out in the zone between the heel and the forefoot. Thus, no measurement may be taken in this area. That, however, makes no difference, as no forces occur there, with a normal foot.

The conductor paths 10 are contacted by conductive elements 14. The conductive elements 14 are continued rectilinearly from the measuring surface proper, in the form of conductor flat cables 24. The continuation is at an angle, obliquely to the rear and toward the heel. This has proved to be especially advantageous, as will be described below.

The six shown conductor paths 10 in the heel zone of the arrangement are connected by conductive elements 14, which pass along the inner side of the foot.

The next three conductor paths 10 in the recessed area 19 (between the heel and the forefoot) likewise are connected to conductive elements 14, substantially at the inner side of the foot. The remaining six front conductor paths 10 are connected by conductive elements 14, which first cross the longitudinal axis of the foot in the recessed area 19, and then pass along the outer side of the foot.

The area of the first three conductor paths 10, in front of the recessed area 19, is pulled out and extends beyond the outer side of the foot.

The rear side of the substrate film 12 (FIG. 1) is provided with shielding areas which are coincident with the conductor paths 10 and consequently, not to be seen in the picture. FIG. 1, however, does show those portions of the shielding areas 17, which project beyond the conductor paths 10 and the conductive elements 14, a non-coincident, but instead, larger-area coverage being provided with all the conductive elements 14. At the outer side of the foot and opposite the same at the inner side of the foot, as well as in the area of the connector flat cable 24, flaps 21, 23 and 31 are provided, which project far beyond the respective conductor elements 14 which are located there.

Figure 2:
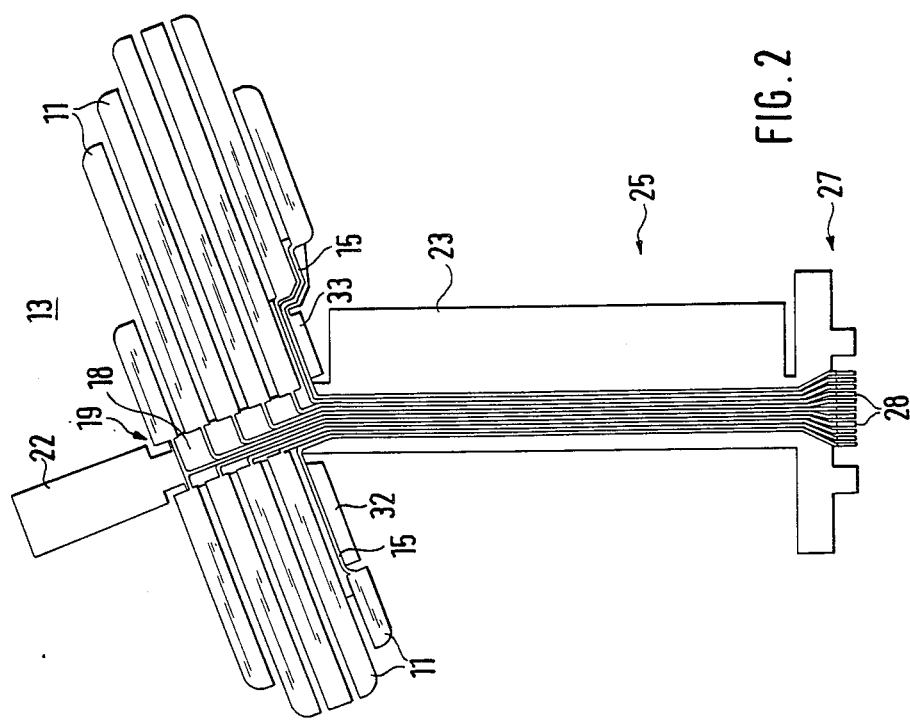
FIG. 2 shows a substrate film after the printing of conductor paths on the same.

The arrangement shown in FIG. 2 differs from the one according to FIG. 1; first, in that the conductor paths 11 are mounted substantially parallel to the longitudinal axis of the foot. Furthermore, the arrangement shown in FIG. 2 has the conductor paths 11 connected to the corresponding conductive elements 15, essentially in the area 19, the area 19 in FIG. 2, corresponding to area 19 of FIG. 1.

Apart from the flaps 23 arranged in the same manner of the connector flat cable 25, the arrangement shown in FIG. 2 comprises three more flats 22, 32 and 33. The flap 22 presents a continuation of the recessed area 19, and the flaps 32 and 33 project beyond the conductive elements 15 passing there.

Figure 4:
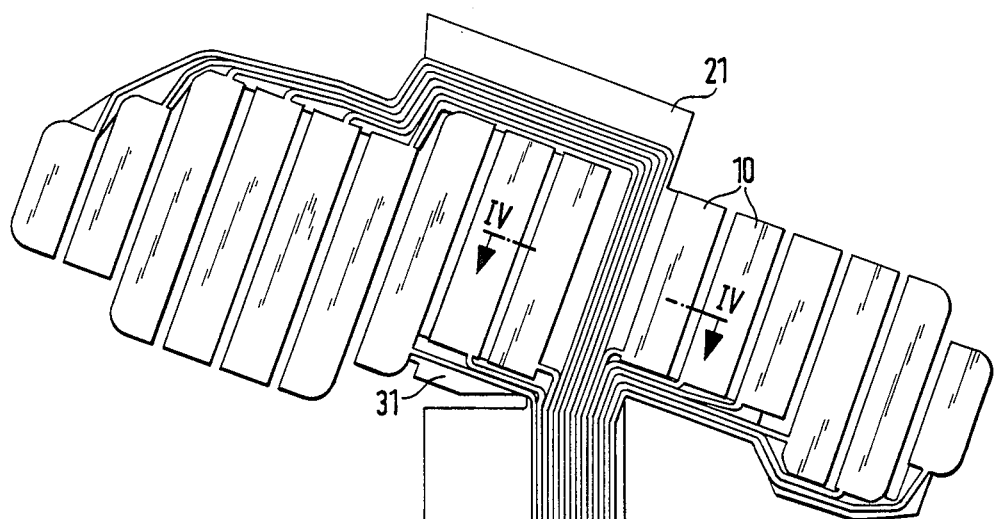
FIG. 4 is a cross-sectional view taken along line IV—IV of FIG. 3.
Figure 4:
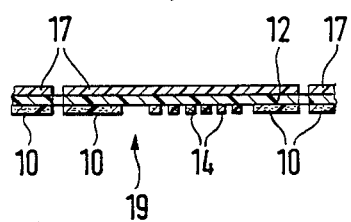
Figure 3:
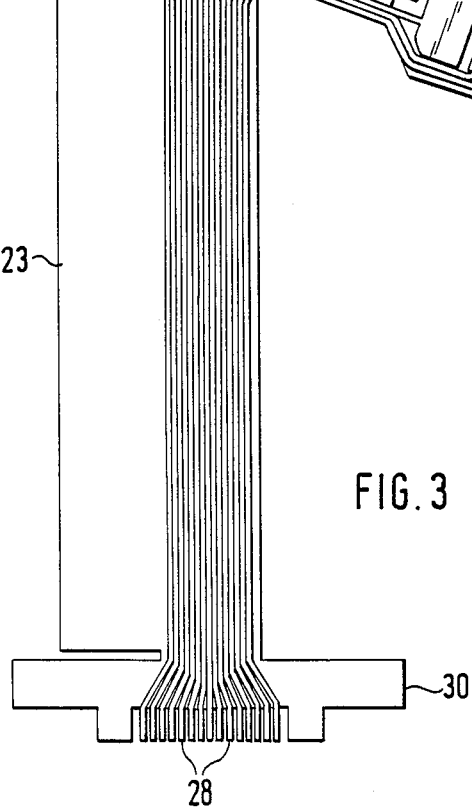
FIG. 3 shows a cut-out substrate film with conductor paths as may be made for the sheeting shown in FIG. 1.

The imprinting of the substrate sheeting is followed by cutting out substantially along the outer contours of the printed shielding areas. This results in the structure explained in FIGS. 3 and 4, which show that the film was not out between the conductor paths 10. FIG. 4 further shows that the shielding areas 17 cover both the conductor paths 10 and the conductive elements 14 from the rear side of the substrate film 12, so that they can shield them from interference.

Once the "excess" substrate film has been cut off, the flaps 21, 23, 30 and 31 are folded over inwardly in the direction of the conductive elements 14 extending there, and then they are bonded on the same. The bonding preferably is effected by way of a carrierless acrylic adhesive tape, as this has proved to be not only especially firm, but also especially convenient in connection with the materials used and the accurate dimensioning of the adhesive faces. The film explained in FIG. 2 is subjected to the same procedure, and this leads to the configuration shown in FIG. 6.

Another striking aspect of FIG. 6 is that the recessed area of the configuration is covered by the shielding area of the flap 22, which is folded over and adhered. This is not the case with the recessed area shown in FIG. 5.

FIGS. 6–8 disclose yet another essential detail relating to the end zones 26 and 27 of the connector flat cables 24 and 25, respectively. The end zones are designed such that the flat cables 24 and 25 can each be connected to a plug by means of which the arrangement can be connected to measuring electronics (not shown).

The illustration of FIG. 7 makes it clear that the substrate film 13, with the conductive elements 15 located (printed) on the same, is folded back inwardly symmetrically from the edge so that the conductive elements 15, at first, will be totally enclosed by the substrate film 13. However, as the substrate film 13 in this portion which lies in the range of section VII—VII is connected continuously to a shielding area, here serving as plug shield 30, the conductive elements 15 are thus shielded all around. The shielding is thus effected in an extremely simple, and yet effective, manner.

In the outermost end portions thereof, the conductive elements 14 and 15, respectively, are spread out to form connector contacts 28 where a plug may be attached. Such plugs are conventional commercial articles, and are used, for instance, for direct plug connection to boards. The connector contacts 28 likewise are applied (identically) by printing and differ from the conductor paths 10 and 11, and the conductive elements 14 and 15 only in regard to their function and their arrangement.

As shown in FIG. 8, a stiffening area 29 of a stiffer synthetic resin sheet is applied at the rear side of the substrate film 13 in the area of the connector contacts 28. Again, it is applied by bonding, preferably by means of a carrierless acrylic adhesive tape. This stiffening permits the particularly safe introduction into the plug without any risk.

Figure 5:
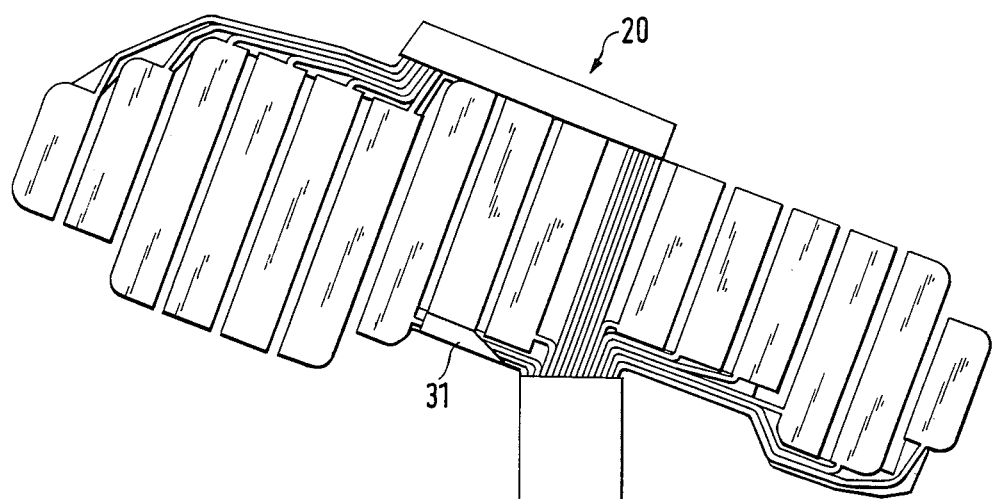
FIG. 5 shows an arrangement according to FIG. 3, including shielding areas which are folded back.
Figure 5:
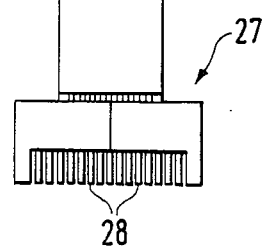
Figure 9:
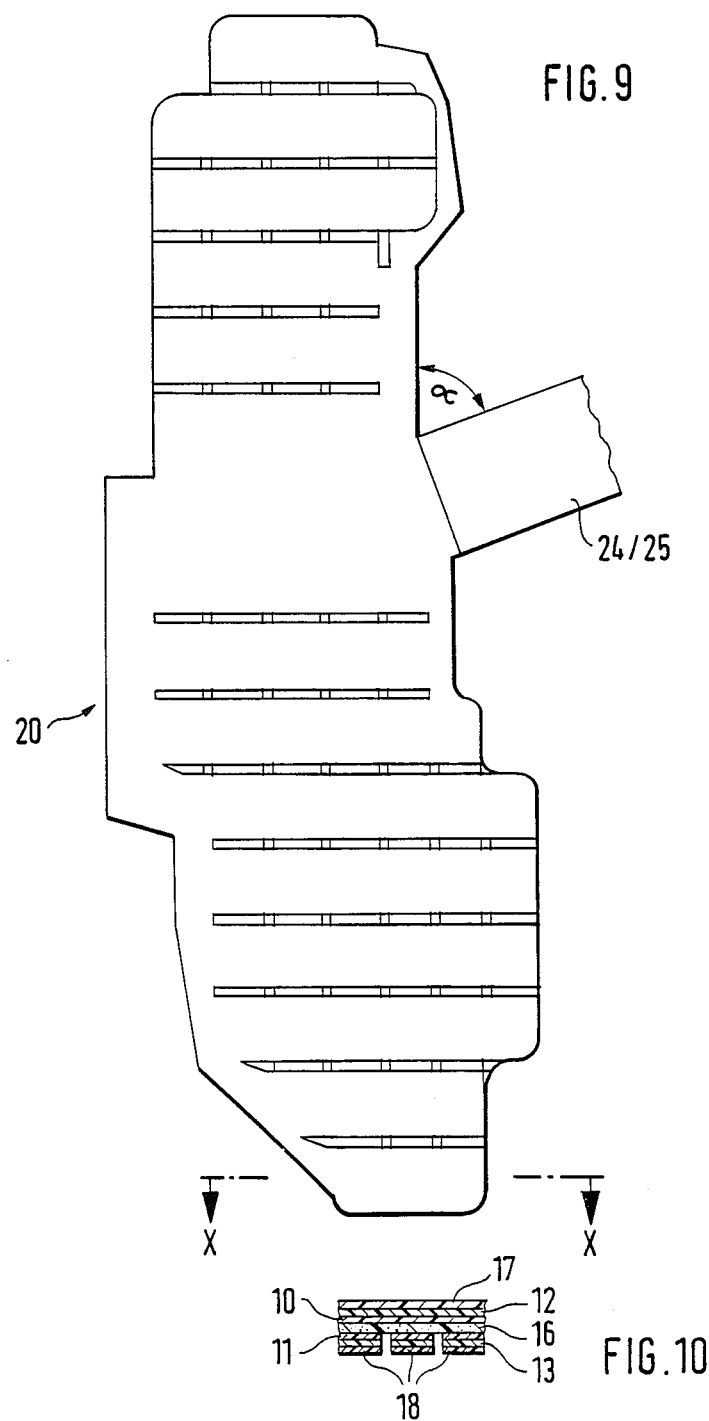
FIG. 9 shows a finished measuring surface.
Figure 10:
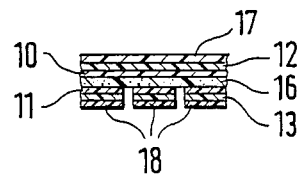
FIG. 10 is a cross-sectional view taken along line X—X in FIG. 9.

After having made the configurations with flaps folded back, shown in FIGS. 5 and 6 and explained above, these arrangements are bonded on opposite sides of a correspondingly cut elastomer layer 16, with the shielding areas 17 and 18 directed outwardly, as illustrated in FIGS. 9 and 10. The intermediate elastomer layer 16 is comprised preferably of a foamed synthetic resin characterized by low hysteresis.

Figure 11:
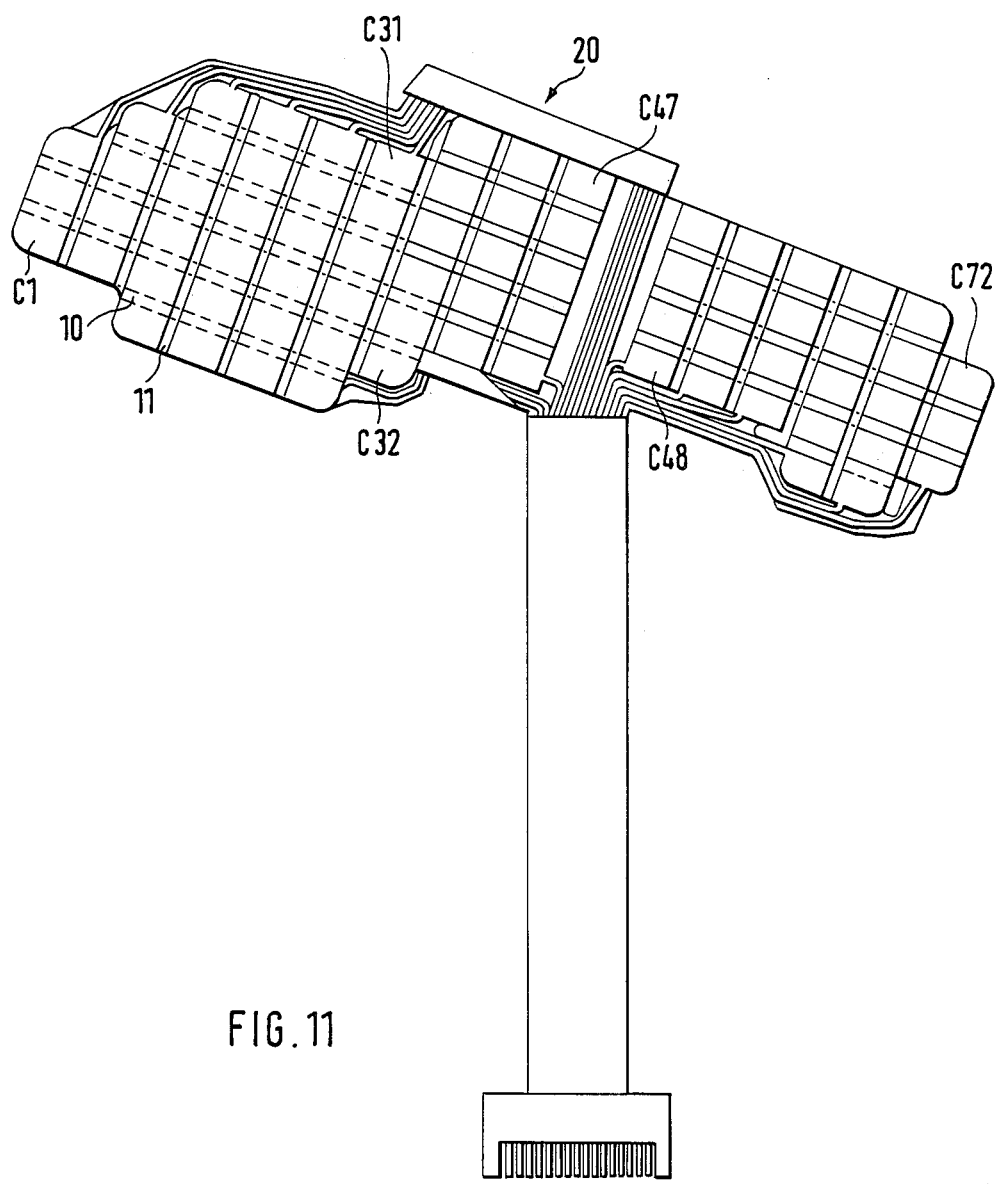
FIG. 11 shows an arrangement according to FIG. 9, the upper shielding areas, as seen in top plan view, being omitted.

As may be gathered from FIGS. 10 and 11, the known matrix arrangement, per se, is obtained in this manner, and it includes capacitor elements Cl to C72. Each of these capacitor elements Cl to C72 may be "dialed", as is known from the publications cited initially. It should be noted with respect to FIG. 11 that this illustration merely serves to explain the capacitor arrangement so as to show the matrix type structure in greater detail.

If the finished "measuring insole" shown in FIG. 9 is to be placed in a shoe, the connector flat cables 24, 25 and the projecting area 20 at the outer side of the foot are folded upwardly. Special advantage is obtained in this context from the angle designated α in FIG. 9. This is the angle at which the flat cables 24 and 25 are inclined rearwardly in the direction of the heel, and makes it possible to pass the measuring cables 24 and 25 out of the shoe without bending or tensioning them.

By virtue of the fact that the area 20 is folded upwardly, any influence of the conducting capacities of the conductive elements 14 and 15 in this area is excluded because only minor forces can occur there during running or walking.

Another preferred embodiment will now be described with reference to FIGS. 12–14. FIG. 12 shows a top plan view of one side of a printed elastomer sheet; FIG. 13 shows the other side thereof; while FIG. 14 is a partial sectional elevational view of a device composed of an element according to FIGS. 12 and 13.

As can be seen from the drawings, a single elastomer layer is provided forming, in its central portion, the elastically deformable dielectric 116, on which the capacitor elements 110 and 111 are printed (on one side each). The relative position of the capacitor elements 110 and 111 with respect to one another is thus firmly defined. The two end portions of the film may be bent with respect to the middle portion at bending lines Ll and L2, so that each end portion can be folded back with its surface onto a surface of the middle portion. The end portions constitute substrate films 112 and 113, and have leads 114 and 115 associated with the respective capacitor elements 110 or 111, as will be explained below.

The leads extend all the way to the edge of the elastomer film, terminating in through contacts 40 and 40' within the elastomer film, the through contacts having a surrounding margin on the surface of the elastomer film opposite the leads 114 and 115.

If the area 112 of FIG. 13 is folded (out of the plane of the drawing) onto the area 116, so that the through contacts 40' will come to lie on the capacitor elements 111, and the area 113 is folded (in FIG. 13 into the plane of the drawing) onto the area 116, so that the through contacts 40 will come to lie on the capacitor elements 110, the result will be a three-layer arrangement, as shown in section in FIG. 14. The fact alone that the through contacts 40, 40' rest on the corresponding capacitor elements 110, 111, affords a rather reliable contact of the leads 114, 115 to the capacitor elements 110, 111. The contacting may be improved by applying conductive adhesive substances on the surrounding margins of the through contacts 40, 40', prior to the folding and fixing of the superposed layers.

In another preferred embodiment of the invention, not presented here in illustrations, the three areas are not connected from the very beginning (along bending lines L1, L2), but rather, are separate areas that are later connected and then superimposed on each other. This embodiment is also especially well suited for making a measuring device in the form of an insole, as described above.

In the case of another preferred embodiment of the invention shown in FIG. 15, the capacitor elements 110 and 111 each are printed on separate substrate films 112 and 113. The respective leads 114 and 115 thereon are printed on the respective outer sides of the substrate films 112 and 113, and are connected to the associated capacitor elements 110 and 111 by through contacts 40 and 40'. These two printed substrate films 112 and 113 are bonded (as shown with the first embodiment described above) on an elastomer layer 116, which presents the dielectric. In this assembly, the capacitor elements 110 and 111 are facing inwardly. This arrangement can also be realized in the multilayer technique known from the production of base plates for printed circuits.

It follows from the above that the instant invention, on the one hand, provides a finished measuring mat or insole for measuring the areal distribution of compressive forces, and, on the other hand, a method of making such a device. It is an essential aspect that the specific design, both of the conductor path and its lead by way of conductive elements, and the specific design of the shielding areas turn out a structure which is especially well protected against electrical interference, and which permits especially accurate measurements to be taken. The production is simple, and may be made in a large series at low cost because, contrary to the opinion held so far by those skilled in the art, ho special design of the conductor paths is required.

The features described above are claimed as essential to the invention, both individually and in any combination.

Having described specific preferred embodiments of the invention with reference to the accompanying drawings, it will be appreciated that the present invention is not limited to those precise embodiments, and that various changes and modifications can be effected therein by one of ordinary skill in the art without departing from the scope or spirit of the invention as defined in the appended claims.

What is claimed is:

1. A device for measuring the areal distribution of compressive forces acting substantially perpendicularly on a deformable measuring surface, comprising:
   an elastically deformable dielectric;
   a plurality of force detector means, each including a capacitor, each capacitor being constituted by capacitor elements, a first group of said capacitor elements being arranged on one surface of said elastically deformable dielectric and a second group of said capacitor elements being arranged on a second surface of the elastically deformable dielectric, such that each capacitor is formed at a point of intersection of capacitor elements from the first and second groups, thereby forming a matrix arrangement of force detector means;
   leads for connecting the groups of capacitor elements to an electronic evaluating device; and
   plastic substrate films, with the capacitor elements being printed, together with the leads, on said plastic substrate films;
   the capacitor elements and the leads being mounted on opposite sides of each substrate film and interconnected in predetermined fashion by through contacts, the through contacts comprising interior linings of recesses extending through the substrate films, which linings are made of the same material as the capacitor elements and leads.

2. The device as claimed in claim 1, wherein the substrate films include an elastomer.

3. The device as claimed in claim 2, wherein the elastomer includes PVC sheeting.

4. The device as claimed in claim 2, wherein the substrate films include a foamed elastomer.

5. The device as claimed in claim 1, wherein the leads and the capacitor elements are formed from a metal-filled synthetic resin.

6. The device as claimed in claim 5, wherein the metal-filled synthetic resin includes silver.

7. The device as claimed in claim 1, wherein the elastically deformable area-type dielectric comprises a layer of a foamed elastomer and the capacitor elements are fixed on the elastically deformable area-type dielectric, with the substrate film directed toward the outside.

8. The device as claimed in claim 7, wherein the substrate films are bonded on the elastically deformable dielectric.

9. The device as claimed in claim 1, wherein the capacitor elements are distributed to several substrate films with an interposed elastically deformable area-type dielectric between superposed adjacent substrate films, the capacitor elements being arranged such that they form a continuous measuring surface, as seen in projection one above the other.

10. The device as claimed in claim 1, wherein shielding areas are printed on the substrate films on a side opposite the capacitor elements so as to cover an area at least equal to that covered by the capacitor elements and the leads.

11. The device as claimed in claim 1, wherein the substrate films are cut transversely between the capacitor elements.

12. A device for measuring the areal distribution of compressive forces acting substantially perpendicularly on a deformable measuring surface, comprising:
   an elastically deformable dielectric;
   a plurality of force detector means, each including a capacitor, each capacitor being constituted by capacitor elements, a first group of said capacitor elements being arranged on one surface of said elastically deformable dielectric and a second group of said capacitor elements being arranged on a second surface of the elastically deformable dielectric such that each capacitor is formed at a point of intersection of capacitor elements from the first and second groups, thereby forming a matrix arrangement of force detector means; leads for connecting the groups of capacitor elements to an electronic evaluating device;
   plastic film substrates, with the capacitor elements being printed, together with the leads, on said plastic film substrates; and the device having a shape of a foot for insertion into a shoe of a test person;

wherein the foot has a longitudinal axis, the capacitor elements are arranged in rows, the first group of capacitor elements extends transversely of the longitudinal axis of the foot, the second group of capacitor elements extends parallel to the longitudinal axis of the foot, and the leads in the area of the tuberositas ossis navicularis are adapted to be passed out of the shoe, together with a strip of substrate film, to form a connector flat cable; and wherein the capacitor elements which extend parallel to the longitudinal axis of the foot extend throughout substantially the full length of the foot and are severed in the area between the heel and the forefoot to form ends by which they are connected to the leads.

13. The device as claimed in claim 12, wherein no capacitor elements extending transversely of the longitudinal axis of the foot are provided in the group of capacitor elements extending transversely of the longitudinal axis of the foot, in the area which lies opposite the area between the ends of the capacitor elements extending parallel to the longitudinal axis of the foot, and wherein at least part of the leads for connecting the capacitor elements in this area are passed toward the outer side of the foot, crossing the longitudinal axis of the foot.

14. A device for measuring the area distribution of compressive forces acting substantially perpendicularly on a deformable measuring surface, comprising:

an elastically deformable dielectric;

a plurality of force detector means, each including a capacitor, each capacitor being constituted by capacitor elements, a first group of said capacitor elements being arranged on one surface of said elastically deformable dielectric and a second group of said capacitor elements being arranged on a second surface of the elastically deformable dielectric such that each capacitor is formed at a point of intersection of capacitor elements from the first and second groups, thereby forming a matrix arrangement of force detector means; leads for connecting the groups of capacitor elements to an electronic evaluating device;

plastic film substrates, with the capacitor elements being printed, together with the leads, on said plastic film substrates; and the device having a shape of a foot for insertion into a shoe of a test person;

wherein leads at an outer side of the foot are passed to capacitor elements extending transversely of the longitudinal axis of the foot in the area of the toes of the foot and these leads are arranged to project outwardly beyond the outer side of the foot, together with the substrate film, in the area of the cuboid for upward folding in this area.

15. The device as claimed in claim 14, wherein a shielding area is disposed on the substrate film on the side opposite the capacitor elements and the leads and the shielding area is extended farther to the outside in the outwardly projecting area so as to form a first flap which is adapted to be folded back inwardly so as to cover the leads and be bonded on the leads with the substrate film positioned therebetween.

16. The device as claimed in claim 13, wherein shielding areas are provided on the side of the substrate film opposite the leads and the capacitor elements and are extended farther to the outside in an extension of the area between the ends of the capacitor elements extending parallel to the longitudinal axis of the foot so as to form a second flap which is adapted to be folded back inwardly onto the area between the ends and to be bonded on the leads with the substrate film positioned therebetween.

17. A device for measuring the areal distribution of compressive forces acting substantially perpendicularly on a deformable measuring surface, comprising:

an elastically deformable dielectric;

a plurality of force detector means, each including a capacitor, each capacitor being constituted by capacitor elements, a first group of said capacitor elements being arranged on one surface of said elastically deformable dielectric and a second group of said capacitor elements being arranged on a second surface of the elastically deformable dielectric such that each capacitor is formed at a point of intersection of capacitor elements from the first and second groups, thereby forming a matrix arrangement of force detector means; leads for connecting the groups of capacitor elements to an electronic evaluating device;

plastic film substrates, with the capacitor elements being printed, together with the leads, on said plastic film substrates; and the device having a shape of a foot for insertion into a shoe of a test person;

wherein the foot has a longitudinal axis, the capacitor elements are arranged in rows, the first group of capacitor elements extends transversely of the longitudinal axis of the foot, the second group of capacitor elements extends parallel to the longitudinal axis of the foot, and the leads in the area of the tuberositas ossis navicularis are adapted to be passed out of the shoe, together with a strip of substrate film, to form a connector flat cable; and wherein shielding areas are provided on the surface of the substrate films opposite the capacitor elements and the leads and the shielding areas are formed to project beyond the leads in the area of the connector flat cable so as to form a third flap which is adapted to be folded back and bonded on the leads with the substrate film positioned therebetween.

18. The device as claimed in claim 12, wherein the connector flat cable has distal ends including connector contacts suitable for mounting of a commercial direct plug connector.

19. A device for measuring the areal distribution of compressive forces acting substantially perpendicularly on a deformable measuring surface, comprising:

an elastically deformable dielectric;

a plurality of force detector means, each including a capacitor, each capacitor being constituted by capacitor elements, a first group of said capacitor elements being arranged on a second surface of the elastically deformable dielectric such that each capacitor is formed at a point of intersection of capacitor elements from the first and second groups, thereby forming a matrix arrangement of force detector means; leads for connecting the groups of capacitor elements to an electronic evaluating device;

plastic film substrates, with the capacitor elements being printed, together with the leads, on said plastic film substrates; and the device having a shape of a foot for insertion into a shoe of a test person;

wherein the connector flat cable has distal ends including connector contacts suitable for mounting of a commercial direct plug connector; and wherein a stiffening sheet is bonded on the substrate film in the area of the connector contacts.

20. A device for measuring the areal distribution of compressive forces acting substantially perpendicularly on a deformable measuring surface, comprising:

an elastically dielectric;

a plurality of force detector means, each including a capacitor, each capacitor being constituted by capacitor elements, a first group of said capacitor elements being arranged on one surface of said elastically deformable dielectric and a second group of said capacitor elements being arranged on a second surface of the elastically deformable dielectric such that each capacitor is formed at a point of intersection of capacitor elements from the first and second groups, thereby forming a matrix arrangement of force detector means; leads for connecting the groups of capacitor elements to an electronic evaluating device;

plastic film substrates, with the capacitor elements being printed, together with the leads, on said plastic film substrates; and the device having a shape of a foot for insertion into a shoe of a test person;

wherein the foot has a longitudinal axis, the capacitor elements are arranged in rows, the first group of capacitor elements extends transversely of the longitudinal axis of the foot, the second group of capacitor elements extends parallel to the longitudinal axis of the foot, and the leads in the area of the tuberositas ossis navicularis are adapted to be passed out of the toe, together with a strip of substrate film, to form a connector flat cable; and wherein the connector flat cables are passed out slightly-inclined in the direction of the heel of the foot.

* * * * *